(12) United States Patent
Olmos et al.

(10) Patent No.: US 7,467,746 B2
(45) Date of Patent: Dec. 23, 2008

(54) MAGNETICALLY ACTIVATED GUIDING DEVICE AND METHOD

(76) Inventors: Pete Olmos, 1370 Los Coches Ct., Chula Vista, CA (US) 91910; Steve Stingl, 1718 Bridlevale Rd., Chula Vista, CA (US) 91913; Thomas Wilson, 23847 Humiston Way, Ramona, CA (US) 92065

( * ) Notice: Subject to any disclaimer, the term of this patent is extended or adjusted under 35 U.S.C. 154(b) by 411 days.

(21) Appl. No.: 11/168,019

(22) Filed: Jun. 27, 2005

(65) Prior Publication Data
US 2006/0289624 A1    Dec. 28, 2006

(51) Int. Cl.
*G06K 7/02* (2006.01)
*A45B 7/00* (2006.01)

(52) U.S. Cl. .......................................... 235/449; 135/65
(58) Field of Classification Search ................. 235/449; 135/65, 66; 340/944
See application file for complete search history.

(56) References Cited

U.S. PATENT DOCUMENTS 4,712,003 A    12/1987    Ban et al.
5,917,326 A    6/1999    Gonzalez et al.
6,964,244 B2 *    11/2005    Stockton ................... 116/205

FOREIGN PATENT DOCUMENTS

| DE | 10246194 | 4/2004 |
|----|----------|--------|
| FR | 2628968 | 9/1989 |
| JP | 60134308 | 7/1985 |
| WO | WO 3039431 | 5/2003 |

\* cited by examiner

*Primary Examiner*—Jamara A Franklin
(74) *Attorney, Agent, or Firm*—Donn K. Harms

(57) ABSTRACT

A guiding device and method to provide information about a path traveled by a user. The device features a cane having a magnet mounted on a distal end. The magnet is attracted to a magnetic pathway formed on a walking surface by a buried cable or applied surface. Nodes positioned at points or intersections along the magnetic path have magnetic switches triggering a broadcast of additional information to the user concerning the magnetic path at the triggered node and along any divergent magnetic paths extending from the node. The device and method can be used to aid visually impaired and even sighted people around areas of residence such as homes and hotels, and public places such as airports and zoos.

18 Claims, 3 Drawing Sheets

MAGNETICALLY ACTIVATED GUIDING DEVICE AND METHOD

FIELD OF THE INVENTION

This device and method herein disclosed relates generally to guiding systems for visually impaired persons as well as those who may suffer from other dysfunctional conditions such as illiteracy or dyslexia. More particularly the present invention relates to a cane based magnetically actuated system for providing spatial, locational and other types of information to visually impaired or other persons.

BACKGROUND OF THE INVENTION

The difficulties encountered by the ten million visually impaired individuals in the United States with regard to spatial navigation are well known. Finding one's way through a bus or train station or an airport, for example, is a dramatic challenge to such a person. This navigation problem which is greatly magnified when there is a need to find a specific gate, a restroom or an agreed to meeting place. Schools, amusement parks, hiking trails, homes, hotels, residential areas, and even common sidewalks present similar difficulties to blind or otherwise visually impaired individuals.

Sighted individuals can rely on visual aids such as indicia on signs to plot paths between known and unknown places, to identify street locations, locate exits, or to determine the destination of a public transport vehicle. Consequently, this ability is generally taken for granted within the mind set of the general population and in the process of the facility design for traverse by the general population.

For the visually impaired, especially the blind, necessary facilities within residential and commercial buildings such as elevators, restrooms, escalators, or stairs have to be remembered by rote learning after repetitive trials or searched for exhaustively with the assistance of an obstacle avoidance device such as a cane, or otherwise found by asking passers by. Similar impediments to walking occur to the visually impaired in homes, trailers, hotels, and virtually any residential or commercial environment. These types of impediments not only greatly increase personal suffering and stress from what should be simple journeys, but also directly contribute to financial inequalities.

Such inequity is evidenced by the fact that only twenty-six percent of visually impaired persons are employed due to the reduced potential for searching for, and holding employment, which is generally located some distance from their place of residence. Travelers with cognitive disabilities such as dyslexia, illiteracy or retardation have similar reductions with regard to such quality of navigation. Even though the Americans with Disability Act of 1990 mandated equal access to transit and public buildings for disabled groups, the problem is far from being resolved. To date, not all street corners have curb cuts, nor do all buildings have access ramps. Further, while not all elevators or bathrooms easily lend themselves for use by wheel-chaired persons, substantial steps have been made in the public domain to meet the needs of the estimated one million U.S. wheelchair users.

Very little has been done to mitigate the trials of the ten million visually impaired persons in traveling during their daily lives. Further, little has been accomplished for the even greater numbers of those others with similar handicaps such as dyslexia, mental retardation, unfamiliarity with the language, or illiteracy, which reduces their easy access to information needed during travel or in other activities where directions are important.

As shall be seen, prior art has many examples that propose to resolve this situation. Such aids include simple devices such as a basic cane with a red tip, to others which employ buried electronic or magnetic cables or spikes and magnetic sensors. More elegant remedies have been proposed employing radar, sonar or infra-red emanations or other electrical effects to convey primarily spatial information. All fall short in that they generally consider only one component of travel. Such art appears limited to that of forward direction and course maintenance as shall be seen below in selected examples.

DESCRIPTION OF PRIOR ART

U.S. Pat. No. 4,712,003 (Itsuki Ban, Yuji Mitsuta; 1987) teaches a blind person guide device comprising a walking stick with an infrared emitting source mounted on the front face. A photoelectric receiving element also is provided on the front face. An internal electronic circuit which uses differences in amplitude and frequency inputs from the photoelectric interface to calculate and communicate distance information via a vibrator in the handle which changes in frequency based on distance to the target object illuminated. This device provides only information related to the distance to or from an object in the path of the beam and no other situationally relevant clues. Further it is expensive and potentially disabled due to the reliance on line of sight for the required infrared light.

U.S. Pat. No. 5,917,326 (Gonzalez, Patten; 1999) depicts an apparatus using at least two permanently magnetized regions embedded in a substrate to be affixed to a surface like a floor. The substrate is employed in combination with a sensor mounted upon a cane or stick capable of detecting the differences in the magnetic fields produced by the magnetic regions. The substrate may also contain variations in texture and color to communicate additional locational detail to those marginally sighted individuals. The device could use also aural or tactile means to interact with the user. As with the previous device, this proposal provides only fundamental spatial information for visually impaired individuals and makes no provision for other classes of disability. Further, the magnetized regions pose a problem if they become demagnetized or come into contact with credit cards, computer disks, or computers or cell phones which can come into their proximity.

International Patent No. PCT/GB02/05040 describes an apparatus intended to aid non-sighted persons to travel in a straight line including a sensing means specific to the direction of travel such as an electronic compass and Hall Effect sensors or an inertial sensor like a gyroscope and a method of communicating to the user that direction such as tactile output through a vibrator. This device as expressed does provide an elegant solution to the problem of straight line compass travel for the visually impaired but does not address any additional informational requirements to the user. Further it is expensive and difficult to implement.

As such, there is an unmet need for a guiding device and method for the blind and visually impaired that is inexpensive to install and simple to operate and navigate. Such a device and method should be of such a simple design and operation that it may be easily deployed on a large and standardized scale. Further, such a device should not rely on line of sight communication due to the potential in public places for blockage or interference with such a system. Still further, such a device and method should not require the blind to employ any additional guiding implements than already used. Most importantly, if it should fail, such a device should allow the blind or visually impaired to continue to use conventional means to guide themselves and therefor not put them in a worse position than before implementing the device. Finally, such a device and system should also be adaptable for providing guiding information to the sighted who might be unfamiliar with a locale or desire the ability to self-tour an area of exploration.

SUMMARY OF THE INVENTION

As can be seen from the above examples there is a need to provide to a disabled or other user not only the means to determine simple directional information but to enhance the delivery of other situational indications such as recommended pathways to desired destinations, to identify to the user the arrival at specific locations or addresses, to increase the user's awareness of the existence of potential hazards, and to provide to the user other useful details to be utilized during the travel experience.

It is thus the object of the present invention to provide to a disabled user such locale information. In order to provide this capability one preferred embodiment of the guiding device for the disabled would consist of the cane conventionally used by the sight impaired with the addition of a magnetic tip at the distal end of the cane through means of attachment of the magnetic tip to the cane. The magnetic tip is complemented by a magnetically attractive strip or cable that is fixed in position to the walking surface traversed by the user of the cane. This magnetically attractive strip can be permanent in the form of a cable or magnetically attractive member actually installed in the walking surface during construction. Or, it could be temporary or added after construction using means for attachment of the strip to or within a surface like a floor such as adhesives, tapes, caulking or epoxies engaged with magnetically attractive components such as a planar magnetically attractive strip. Finally, in cases where the device is employed to provide secondary information to sighted individuals, say at a museum or amusement park, the magnet can be placed in or on a shoe or some other means to carry it close to the ground so it can be used to activate nodes which would be clearly marked.

The magnetically attractive strip would be generally situated along the paths of travel to guide the user of the cane along a safe path of travel. Additionally, signage, magnetically activated switches and annunciators, GPS locational identifiers, and any other sending or receiving devices can be used to enhance the amount of information about the locale that is communicated to the cane user.

The magnetic pathway would be to designate specific destinations between two points such as the entrance to a building or residence and one or a plurality of rooms in that building. Along more complicated routes with more options of divergence in travel, nodes having magnetically activated switches can be located at each path intersection with another possible path, which generate for the user an aural, visible, or a tactile signal that a decision can be made as to the ultimate destination of travel along one or more divergent paths from an intersection. The signal can be as simple as a vibrator designed to convey to the user arrival or additional directions, or other information pertinent to the user's navigation.

In use, a visually impaired or other user would employ a conventional hand-held cane having a magnetic distal end. When passing the magnetic distal end of the cane over the magnetically active substrate, the user receives immediate tactile "feedback" as to the path in front of them since the magnet will tend to be pulled toward the magnetically attractive component such as a cable or metallic substrate. In the simplest embodiment, as the user moves along he will be guided along a safe path between two points without the need for any other components of the system. The magnetically attractive substrate would traverse the distance between two points such as the entrance to a building and an office frequented by similar users. In this fashion, the user employs the cane they are already familiar with, with the addition of a magnetic attraction for tactile feedback as to the safe or most advantageous route to follow.

As previously noted, additional feedback could be provided by placing magnetically activated switches or "nodes" designed to activate a secondary source of information to the user. The secondary source can be as simple as a vibrator in the cane to tell the user that they are nearing a destination or have arrived or may turn one way or the other at the node. The means for magnetic switching in the node can also initiate other forms of information provision such as signage, and/or to activate speakers with auditory information, and/or user worn receivers for communicating prerecorded information and/or to initiate braille keyboards. Of course other means of communicating supplemental route information to the magnetic attraction along points or nodes in the route can be employed and such is anticipated.

An especially preferred information device activated by the disclosed device would be provided by a small cell phone/GPS/radio receiver and computer for aural and other means of notification which would be worn by the user. The device would be preprogrammed with the users desired paths and destinations such as might be appropriate on a tour of a museum or park. Transmission of information regarding a specific location or route along the path being followed by the user would be triggered by the magnetic interaction of the cane and the magnetically activated switches or nodes located en route which would initiate a broadcast signal when the magnetic tip came into proximity with the node. The signal would be encoded to activate the device worn by the user to provide a specific piece of information about the individual node just activated which would be stored in the user-worn receiver, or transmitted to it based on the node activated. Then the device would inform the user about destination or location information specific to the activation of the specific node.

With respect to the above description, before explaining at least one embodiment of the invention in detail, it is to be understood that the invention is not limited in its application to the details of construction and to the arrangement of the components or steps set forth in the following description or illustrated in the drawings, nor just to buildings. The apparatus and methods of the invention are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing of other structures, methods and systems for carrying out the several purposes of the present disclosed device. It is important, therefore, that the objects and claims be regarded as including such equivalent construction and methodology insofar as they do not depart from the spirit and scope of the present invention.

Further objectives of this invention will be brought out in the following part of the specification, wherein detailed description is for the purpose of fully disclosing the invention without placing limitations thereon.

BRIEF DESCRIPTION OF DRAWINGS

FIG. 5 depicts two magnetic substrates on two side edges of a defined path in-between.

DETAILED DESCRIPTION OF PREFERRED EMBODIMENTS OF THE DISCLOSED DEVICE

Figure 1:
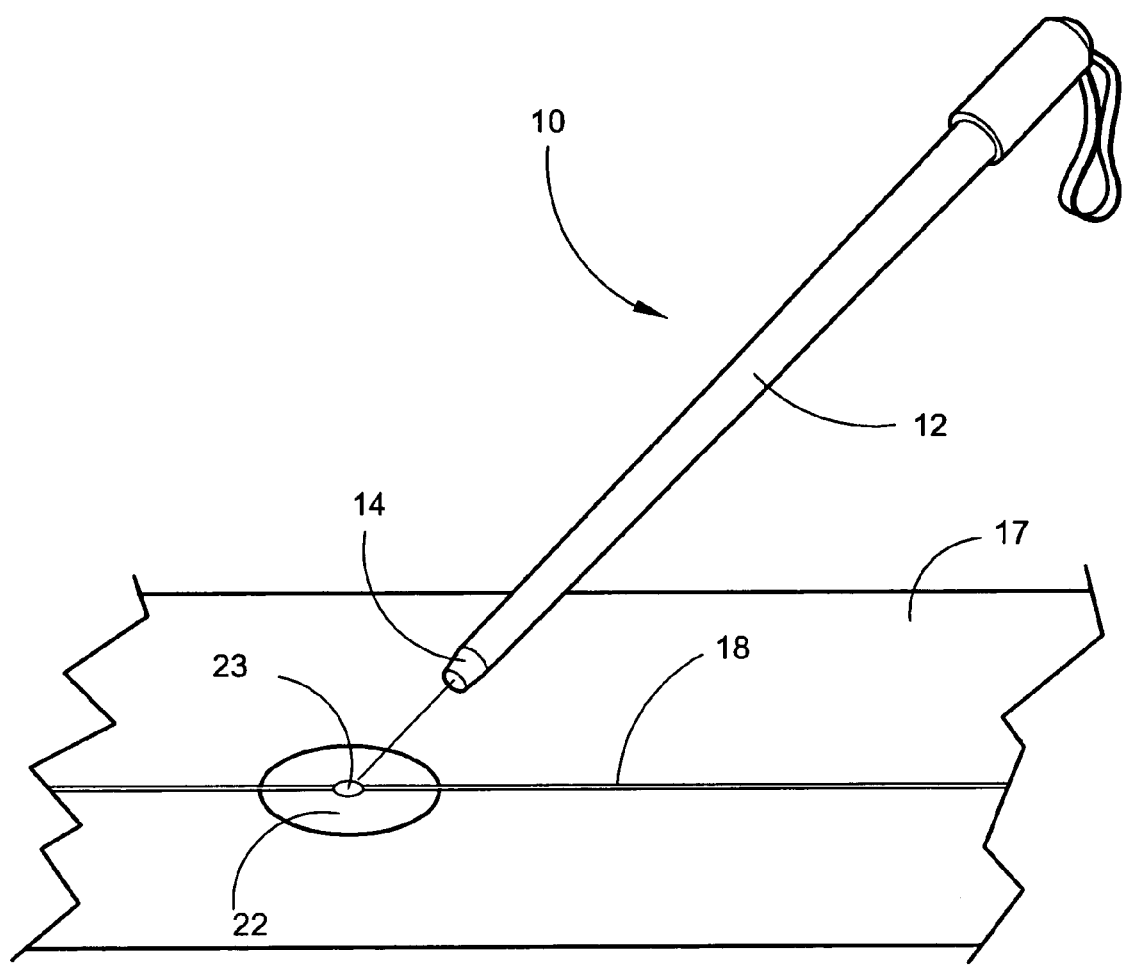
FIG. 1 displays a side view of a preferred embodiment of the device 10 showing a magnetically enhanced cane, magnetically attractive substrate, and optional major components.
Figure 2:
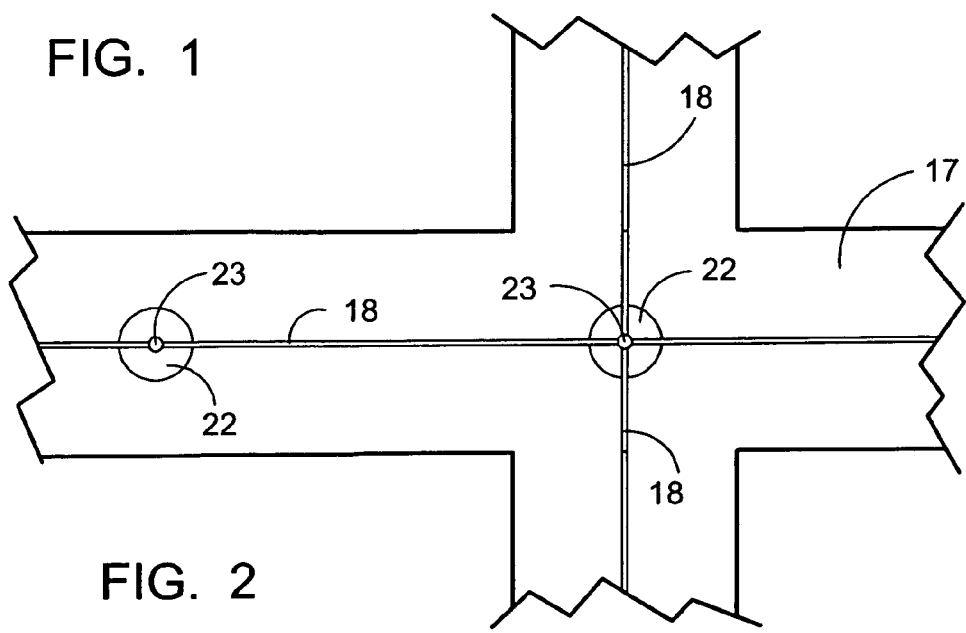
FIG. 2 depicts a cable embodiment of the magnetically attractive pathway.
Figure 3:
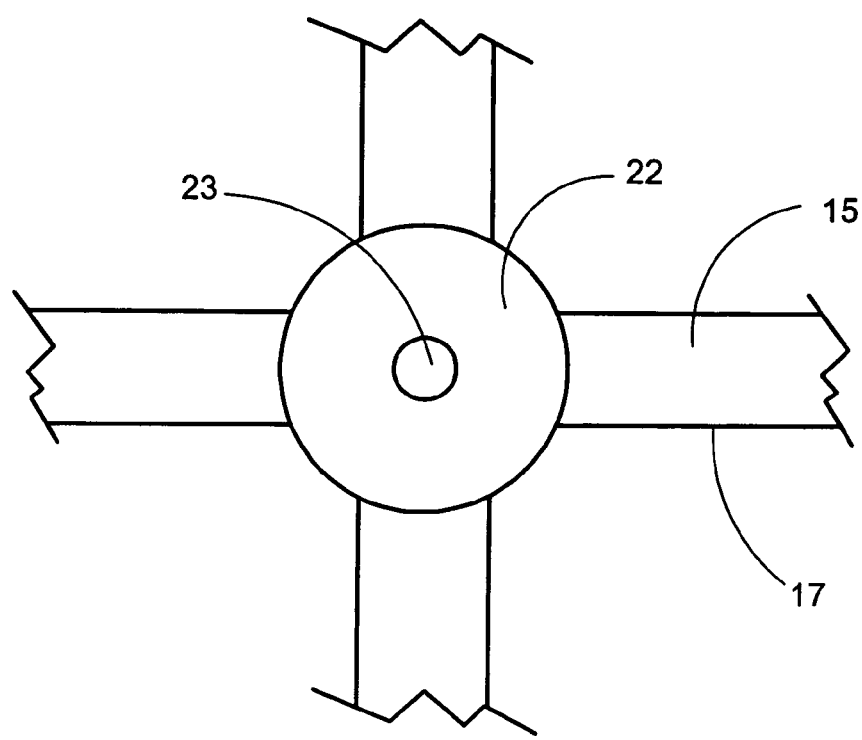
FIG. 3 depicts a planar embodiment of a magnetically attractive pathway.
Figure 5:
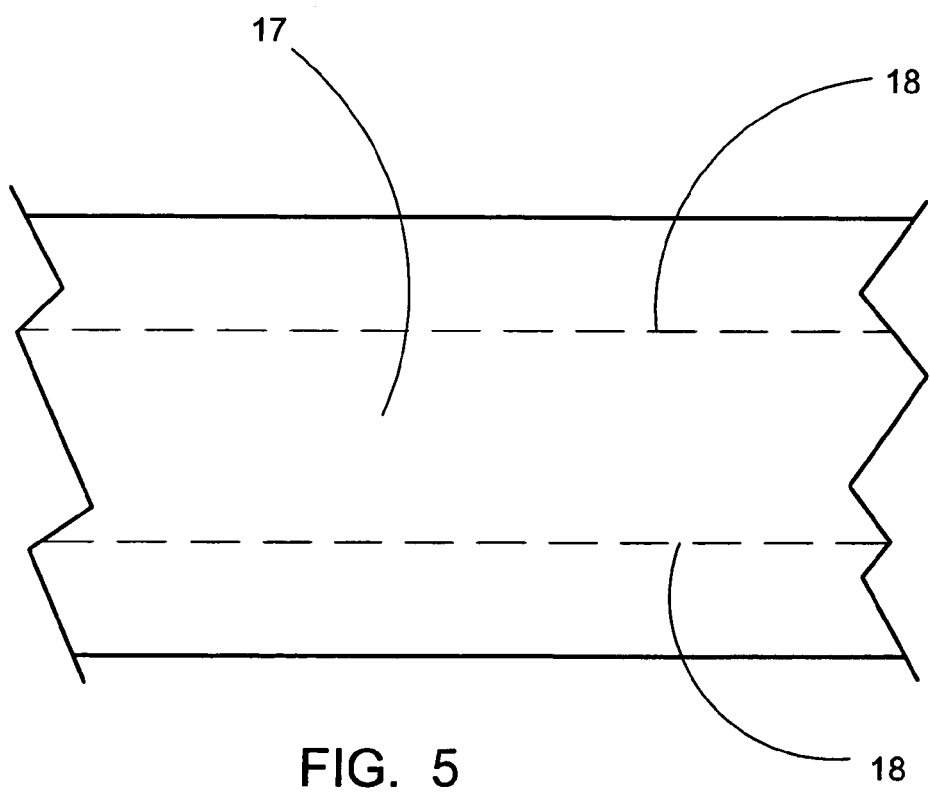

Referring now to the drawings, FIGS. 1-4 disclose the preferred embodiments of the disclosed device 10 and method for defining a magnetically attractive pathway along with optional components to enhance the performance of the device 10. The basic device 10 however will work well without the optional components in a minimum implementation of the device 10. This is especially important if for some reason such as a power failure, the switches, nodes, and means of supplemental route information transmission fail. Consequently, the user 11 can always depend upon the conventional elongated member such as the cane 12 by itself as a means for guidance of the visually impaired. The magnetically attractive pathway 17 consists of at least one, of a group of magnetically attractive pathway components, consisting of at least one cable 18 buried in said walking surface, and a metallic strip or substrate 15 engaged to the walking surface. Where a means for magnetic attraction along a defined path is provided to define a route, such as a magnetically attractive substrate 15 or cable 18, the cane 12 with the affixed permanent magnet 14 providing tactile feedback as the magnet 14 is attracted to the cable 18 or substrate 15 provides a tactile means to discern the route to follow for the user 11.

This allows the user 11 to employ the cane 12 in the normal fashion where no cable 18 or other substrate 15 exist, but to use the cane 12 with the magnet 14 forming a magnetic tip that inherently will follow the cable 18 or other magnetically attractive substrate 15 where it is provided. Thus the user 11 is provided either the same route information available where there is no cable 18 or substrate 15, and enhanced route information where there is a cable 18 or other substrate 15 provided to define the magnetic pathway 17 to be followed.

The device 10 as depicted in FIG. 1 displays a side view of a preferred embodiment with specific attention to the spatial relationships of the main components as conceived. The device 10 employs a component already widely used by the blind in the form of an elongated member such as a staff or cane 12. This cane 12 is enhanced at the distal end with an affixed permanent magnet 14 or similar means for magnetic attraction. The opposite or retention end is employed for gripping or constraint purposes by the user 11. The magnet 14 can be attached permanently or can be removably engaged in case the user 11 wishes to take it off when a substrate 15 or cable 18 or other means to define a continuous magnetically attractive pathway is not provided.

The magnet 14 is shown in use wherein it would come into close proximity to the means for designation of a continuous magnetically attractive pathway 17 formed of a cable 18 or magnetically attractive substrate 15 which can be followed by the user 16. Such a magnetically attractive pathway 17 would be made of a metal which has a ferrous content that is attractive to a magnet 14. Currently, the simplest means for magnetic attraction to provide such a magnetic pathway 17 would be a buried cable 18 which could be cast into the concrete of walkways and buildings when they are built or remodeled thereby forming the appropriate magnetically attractive pathway below the walking surface of the walkway. Or, a planar substrate 15 adherable or otherwise attachable to the walking surface of a floor or walkway can be employed to form the magnetically attractive path 17. Such a substrate would have one or a plurality of magnetically attractive materials encompassed therein to form the magnetically attractive path 17 and would be adhered or otherwise engaged to the walking surface 20. This could be done permanently, or temporarily for special events in the case of the substrate 15.

As noted above, in its simplest form, the device 10 would allow the user to employ the cane 12 with the magnet 14 on the distal end, to follow the magnetically attractive path 17 down a designated path on a sidewalk or building walkway and know they are on a safe path. One pathway in the middle of the designated path can be provided for the magnet 14 enabled cane 12 to follow. Or, a pair of magnetically attractive strips could be provided on both side edges of a designated pathway so that the user would know the proper path is in-between the pair when the cane 12 is passed between them.

Optionally, in a preferred embodiment of the device, 10, other components may be employed with the system to further enhance the navigational abilities to the users 16. A first preferred enhancement would be the inclusion of nodes 22 as a means to communicate to the user 16 that options for travel are occurring in the defined magnetically attractive pathway being followed. The nodes 22 would employ a magnetically activated means for switching such as a magnetic switch 23 which would initiate secondary actions of the system. Such switches are conventionally available such as the S12 Hall Switch from Sensor Solutions Corporation. The switch 23 would initiate a signal or transmission or otherwise provide a means to signal that a node 22 has been encountered by a user 11 carrying a cane 12 with a magnet 14. The signal would then activate a remote component which provides a means to communicate an option to the user 16 when crossing the specific individual node 22 activated.

In the simplest such secondary action, the switch 23 would be in electrical communication with a transmitter and activate it to transmit a code or signal to the area around the encountered and activated node 22. In the simplest form of provision of secondary information, the signal would activate a vibrator 18 on the cane 12 itself to let the user 16 know they are at an intersection in the path 17. The user, if familiar with the path 17 would know they may proceed in different magnetically attractive diverging directions on the path 17 to different destinations.

If the user 16 were unfamiliar with the path 17, in a particularly favored embodiment, the node 22 would employ either a magnetically tripped switch 23 or an RFID device which would be energized by the magnet 14 itself, to initiate a specific broadcast signal locally, as a means to activate a remote component means for providing a secondary information source specific to the user's 11 options at the specific node 22 so encountered.

The nodes 22 thus would be used to initiate a means for provision of secondary information about the locale of the node 22 through secondary information devices such as a speaker 20 electrically engaged to an amplifier and recorded message which would orally announce a message to the user 11 about the specific node 22 just activated. Or, a special signage 21 could be activated that is readable by a sighted companion or sighted user of the system.

Optionally the node 22 can operate as the means for switching or activating other devices to perform an informational task for the user 11 about the location of and surrounding an activated node 22. Such secondary information providing devices include a radio transceiver which would broadcast preprogramed enhanced directions which would be communicated to the user 11 via the speaker 20 or through headphones connected to a receiver 26 or cell phone which the user 11 would wear. In this manner, when the user swiped the magnet 14 over a node 22, the magnetically activated switching means would cause a message to be broadcast only to the user 11 activating the specific node 22 who would be presented aurally through a speaker or earphone with information concerning the locale of the node 22. The message could contain information about the location of the node 22, the options for the user if he proceeds forward or turns right or left as to destinations along those paths. This would provide users unfamiliar with their locale much more information about their forward destinations following any path that extends in any direction from a node 22.

Figure 4:
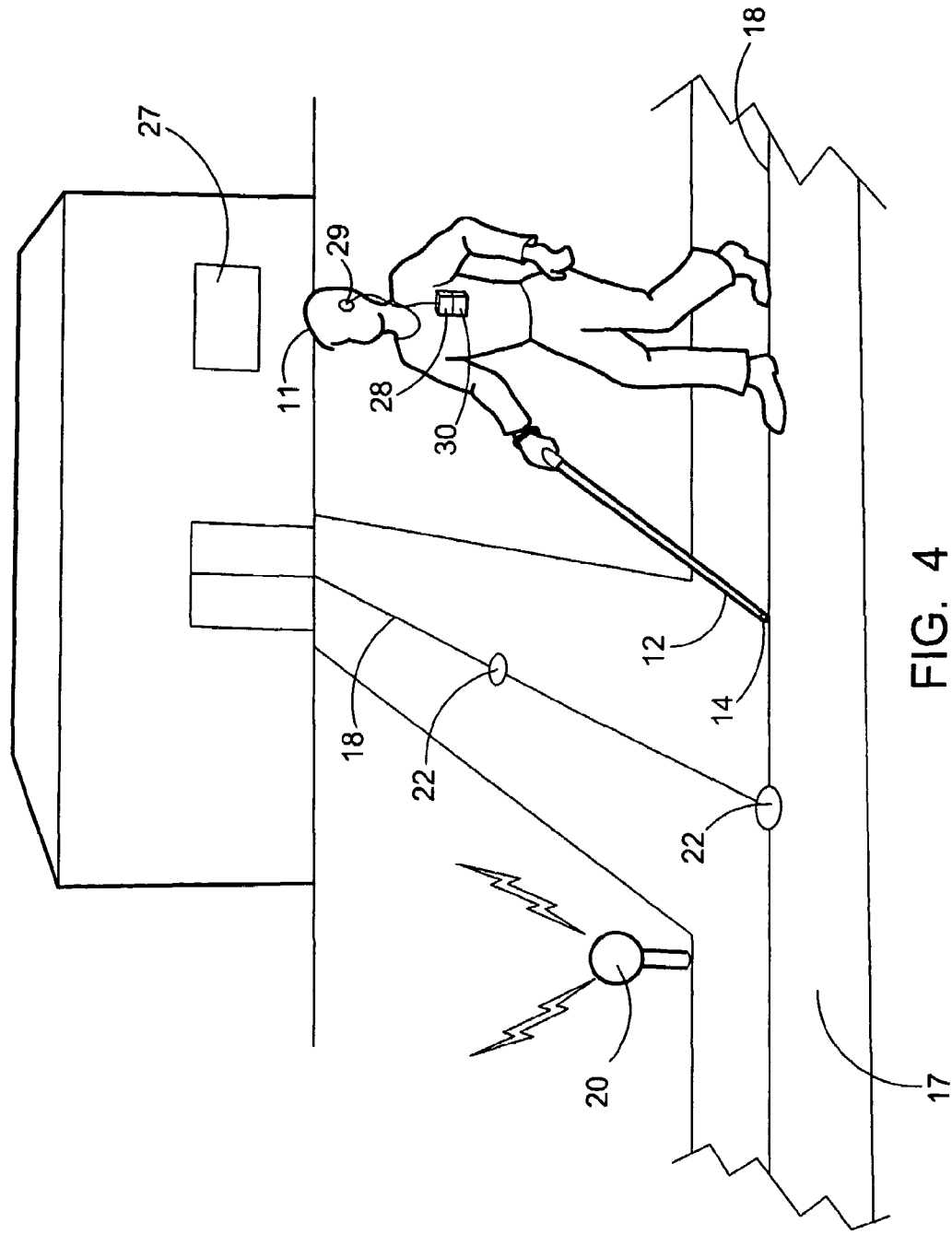
FIG. 4 shows a view of the device in use along a path delineated by the magnetic substrate and a node along the path.

FIG. 4 portrays a view of the device 10 in use and outlines the locations of the pathway 17 and magnetically attractive path 17 provided by the cable 18 or substrate or other continuous means for magnetic attraction along the path. As shown, the user of the cane 12 with the magnetic 14 would follow the buried cable 18 since the magnet would tend to pull the distal end of the cane 12 toward the cable 18. Passing the cane 12 over a node 22 along the path 17 would activate one or a combination of remote components from a group of remote components consisting of a vibrator located on the cane 12 and means to transmit aural communications regarding the specific node 22 just activated. With the vibrator and the means to transmit aural communications, a means for switching 23 which would communicate to a remote or adjacent information storage or broadcast device to provide a predetermined bit of information whenever the node 22 comes into proximity with the magnet 14.

As shown, the magnetically activated switching means controls activation of an amplified speaker 25 or a radio broadcasting device 27 intended to convey information such as an address along the path 17 or an upcoming turn or a destination along the path to the right or left of the node 22. The broadcast device 27 could communicate path information over the speaker 20 adjacent or close to the node 22 or could also communicate the information to a transceiver 28 or a computing device 30 such as a preprogrammed MP3 player, which would store information about node points along the path 17.

In the case of a user worn computing device 30, various information associated with individual nodes 22 could be stored in the computing device 30 memory, and the broadcast device 27 would broadcast a signal locally which would be received by the computing device 30. The signal would contain a digital or analog code as to what node 22 has been triggered, and the computer would communicate the stored information associated with the individual node 22 to the user 16 through speaker 20 or earphones 29 worn by the user 11. With the ever broadening scope of capability and memory being provided by cell phones, the computing device and transceiver can be provided by a cell phone which would communicate transmitted or stored information about the node 22 just triggered to the user 11.

When employed as a method for providing a guiding device for a determined walking path along a walking surface users would be provided with or have their own canes 12 with magnets 14 attached. The person or institution providing the guiding device would do so by placing a magnetically attractive pathway engaged with a walking surface. Thereafter a user may employ a hand-held means to place a magnet 14, adjacent to said magnetically attractive pathway laid down, and will thus be guided along the walking path by the attraction of the magnet to the magnetically attractive pathway engaged with the walking surface. The tactile feedback alone provides the user with information to follow the path. Or the nodes 22 and related remote components and aural means for communication can also be provided along the route.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications, as would occur to those skilled in the art, are considered to be within the scope of this invention as broadly defined in the appended claims.

Further, the purpose of the attached abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

What is claimed is:

1. A guiding device for the visually impaired user comprising:
   a magnet adapted for engagement to a distal end of an elongated member;
   a magnetically attractive pathway engaged with a walking surface;
   said magnetically attractive pathway defining a walking path which is followed by said user; and
   at least one node located along said pathway;
   said node having means to activate a remote component to an informational mode when said magnet is placed adjacent to said node; and
   said remote component in said informational mode communicating information to said user specific to said node so activated to said informational mode;
   whereby a user holding said elongated member with said distal end adjacent to said walking surface, is guided along said walking path by the attraction of said magnet to said magnetically attractive pathway engaged with said walking surface.

2. The guiding device of claim 1 wherein said magnetically attractive pathway is at least one, of a group of magnetically attractive pathways, consisting of at least one cable buried in said walking surface, and a metallic strip engaged to said walking surface.

3. The guiding device of claim 2 additionally comprising:
   a plurality of said nodes located along said pathway;

each of said plurality of said nodes having means to activate a remote component to an informational mode when said magnet is placed adjacent to each said node; and said remote component in said informational mode communicating information to said user specific to each said node so activated to said informational mode.

4. The guiding device of claim 3 wherein said remote component is one or a combination of remote components from a group of remote components consisting of a vibrator located on said elongated member and means to transmit aural communications regarding the specific node activated, to be heard by said user.

5. The guiding device of claim 4 wherein means to transmit aural communications to be heard by said user is one of a group of aural communication transmission devices including a speaker, and a radio transmission device transmitting to a receiver carried by said user; and whereby said user is transmitted an aural communication specific to said node being activated.

6. The guiding device of claim 2 wherein said remote component is a vibrator located on said elongated member.

7. The guiding device of claim 2 wherein said remote component comprises:

means to transmit aural communications to be heard by said user; and said aural communications providing said information specific to said node activating said remote component.

8. The guiding device of claim 7 wherein means to transmit aural communications to be heard by said user is one of a group of aural communication transmission devices including a speaker, and a radio transmission device transmitting to a receiver carried by said user; and whereby said user is transmitted an aural communication specific to said node being activated.

9. The guiding device of claim 2 additionally comprising:

said magnetically attractive pathway extending from a starting point to one or a plurality of destinations through divergent pathways emanating from said node; and said remote component when activated providing information to said user regarding said divergent pathways from said node activating said remote component.

10. The guiding device of claim 1 additionally comprising:

a plurality of said nodes located along said pathway;

each of said plurality of said nodes having means to activate a remote component to an informational mode when said magnet is placed adjacent to each said node; and said remote component in said informational mode communicating information to said user specific to each said node so activated to said informational mode.

11. The guiding device of claim 10 wherein said remote component is one or a combination of remote components from a group of remote components consisting of a vibrator located on said elongated member and means to transmit aural communications regarding the specific node activated, to be heard by said user.

12. The guiding device of claim 11 wherein means to transmit aural communications to be heard by said user is one of a group of aural communication transmission devices including a speaker, and a radio transmission device transmitting to a receiver carried by said user; and whereby said user is transmitted an aural communication specific to said node being activated.

13. The guiding device of claim 10 additionally comprising:

said magnetically attractive pathway extending from a starting point to one or a plurality of destinations through divergent pathways emanating from said node; and said remote component when activated providing information to said user regarding said divergent pathways from said node activating said remote component.

14. The guiding device of claim 1 wherein said remote component is a vibrator located on said elongated member.

15. The guiding device of claim 1 wherein said remote component comprises:

means to transmit aural communications to be heard by said user; and said aural communications providing said information specific to said node activating said remote component.

16. The guiding device of claim 15 wherein means to transmit aural communications to be heard by said user is one of a group of aural communication transmission devices including a speaker, and a radio transmission device transmitting to a receiver carried by said user; and whereby said user is transmitted an aural communication specific to said node being activated.

17. The guiding device of claim 1 additionally comprising:

said magnetically attractive pathway extending from a starting point to one or a plurality of destinations through divergent pathways emanating from said node; and said remote component when activated providing information to said user regarding said divergent pathways from said node activating said remote component.

18. A method for providing a guiding device for a determined walking path along a walking surface, comprising:

placing a magnetically attractive pathway engaged with said walking surface;

positioning at least one node located along said pathway having means to activate a remote component to an informational mode when said magnet is placed adjacent to said node; and employing said remote component in said informational mode communicating information to said user specific to said node so activated to said informational mode; and whereby a user employs a hand held means to place a magnet, adjacent to said magnetically attractive pathway and be guided along said walking path by the attraction of said magnet, to said magnetically attractive pathway engaged with said walking surface.

* * * * *